(12) United States Patent
Dagle et al.

(10) Patent No.: US 8,957,259 B2
(45) Date of Patent: Feb. 17, 2015

(54) DIMETHYL ETHER PRODUCTION FROM METHANOL AND/OR SYNGAS

(75) Inventors: Robert A. Dagle, Richland, WA (US); Yong Wang, Richland, WA (US); Eddie G. Baker, Pasco, WA (US); Jianli Hu, Kennewick, WA (US)

(73) Assignee: Battelle Memorial Institute, Richland, WA (US)

( * ) Notice: Subject to any disclaimer, the term of this patent is extended or adjusted under 35 U.S.C. 154(b) by 0 days.

(21) Appl. No.: 11/241,321

(22) Filed: Sep. 30, 2005

(65) Prior Publication Data

US 2007/0078285 A1    Apr. 5, 2007

(51) Int. Cl.
*C07C 41/09*    (2006.01)
*C07C 41/01*    (2006.01)

(52) U.S. Cl.
CPC ............... *C07C 41/09* (2013.01); *C07C 41/01* (2013.01)
USPC ........................................................ 568/698

(58) Field of Classification Search
USPC ........................................................ 568/698
See application file for complete search history.

(56) References Cited

U.S. PATENT DOCUMENTS

| | | | | |
|---|---|---|---|---|
| 4,011,275 | A * | 3/1977 | Zahner | 518/713 |
| 4,605,788 | A | 8/1986 | Brake | |
| 5,218,003 | A * | 6/1993 | Lewnard et al. | 518/700 |
| 5,821,111 | A * | 10/1998 | Grady et al. | 435/252.5 |
| 6,562,306 | B1 * | 5/2003 | Shikada et al. | 422/223 |
| 6,616,909 | B1 | 9/2003 | Tonkovich et al. | |
| 6,638,892 | B1 * | 10/2003 | Wu et al. | 502/307 |
| 2002/0182735 | A1 * | 12/2002 | Kibby et al. | 436/37 |
| 2003/0219903 | A1 | 11/2003 | Wang et al. | |
| 2004/0005723 | A1 | 1/2004 | Empedocles et al. | |
| 2005/0176832 | A1 * | 8/2005 | Tonkovich et al. | 518/726 |
| 2005/0239910 | A1 | 10/2005 | Jarosch et al. | |

OTHER PUBLICATIONS

Cao et al., "Kinetic studies of methanol steam reforming over PD/ZnO catalyst using a microchannel reactor," *Applied Catalysis A: General*, vol. 262, pp. 19-29 (2004).
Fu et al., "The Effect of Solvent and Mixed Method to Direct Synthesis of DME from Biomass Syngas Via Gasification Bi-Functional Catalyst Preparation," *International Conference on Energy, Environment and Disasters*, Charlotte, North Carolina, 1 pg. (Jul. 24-30, 2005).
Hu et al., "Conversion of Biomass Syngas to DME Using a Microchannel Reactor," *Ind. Eng. Chem. Res.*, vol. 44, pp. 1722-1727 (2005).
Nakato et al., "Changes of Surface Properties and Water-Tolerant Catalytic Activity of Solid Acid $Cs_{2.5}H_{0.5}PW_{12}O_{40}$ in Water," *Langmuir*, vol. 14, pp. 319-325 (1998).
Hofbauer, Hermann et al., "Biomass CHP Plant Güssing—A Success Story," *Expert Meeting on Pyrolysis and Gasification of Biomass and Waste*, Strasbourg, France, Oct. 2002, 13 pages.
Hofbauer and Rauch, "Hydrogen-Rich Gas from Biomass Steam-Gasification," Publishable Final Report, Institute of Chemical Engineering Fuel and Environmental Technology, Getreidemark 9/159, A-1060 Wien, Mar. 31, 2001, 26 pages.

* cited by examiner

*Primary Examiner* — Rosalynd Keys
(74) *Attorney, Agent, or Firm* — Frank Rosenberg; Derek H. Maughan

(57) ABSTRACT

Disclosed are methods for producing dimethyl ether (DME) from methanol and for producing DME directly from syngas, such as syngas from biomass. Also disclosed are apparatus for DME production. The disclosed processes generally function at higher temperatures with lower contact times and at lower pressures than conventional processes so as to produce higher DME yields than do conventional processes. Certain embodiments of the processes are carried out in reactors providing greater surface to volume ratios than the presently used DME reactors. Certain embodiments of the processes are carried out in systems comprising multiple microchannel reactors.

22 Claims, 9 Drawing Sheets

DIMETHYL ETHER PRODUCTION FROM METHANOL AND/OR SYNGAS

ACKNOWLEDGMENT OF GOVERNMENT SUPPORT

This invention was made with Government support under Contract DE-AC0576RLO1830 awarded by the U.S. Department of Energy. The Government has certain rights in the invention.

FIELD

Disclosed herein are processes and systems for producing dimethyl ether from syngas and/or methanol.

BACKGROUND

Biomass feedstock, such as agriculture and forestry residues, plays an important role in developing alternatives to fossil fuels. Although there are several methods of generating energy from biomass, gasification, in which a hydrogen-carbon monoxide gas mixture (syngas) is produced, offers several advantages. For example, syngas, like natural gas, can be burned in gas turbines, which are more efficient than steam boilers. Another key feature of syngas is, like petroleum products, it can be converted to useful chemicals, including dimethyl ether (DME). Syngas is also an available "raw" fuel from sources other than biomass, such as from coal gasification and natural gas stem reforming and other sources.

DME can be used as building blocks for synthesizing important chemicals, including dimethyl sulfate, high value oxygenated compounds, and lower olefins. Because of its environmentally benign properties, it can also be used as an aerosol propellant in products such as hair spray and shaving cream. Recently, DME has been suggested as an alternative fuel for diesel engines. Engine performance tests indicate that DME has thermal efficiencies equivalent to traditional diesel fuel. Other advantages of using DME as a diesel replacement include the reduced $NO_x$ emissions, near-zero smoke production, and less engine noise. However, there are obstacles to producing DME from biomass syngas at an economical scale. For example, unlike petroleum, coal, and natural gas plants, which are established for central, large-scale applications, biomass feedstock and gasification systems are widely distributed geographically. If conventional DME process technology is adopted, a scale of 2500 t/d may be required for production economically comparable to conventional LPG fuel. Because it is difficult to deliver enough biomass to satisfy this criterion using conventional technology, a more compact and efficient portable process for converting the biomass or other source of syngas to DME is needed.

SUMMARY

Disclosed are methods for producing dimethyl ether (DME) from methanol and for producing DME directly from syngas, such as syngas from biomass. Also disclosed are apparatus for DME production. The disclosed processes generally function at higher temperatures with lower contact times and at lower pressures than conventional processes so as to produce higher DME yields than do conventional processes. For example, disclosed are processes for producing dimethyl ether comprising providing a source of methanol, providing a catalyst, reacting the methanol and the catalyst at a temperature from about 200° C. to about 500° C. with a contact time of from about 15 milliseconds to about 250 milliseconds, at about 1 atm to about less than 9 atm, and producing greater than about 70% yield (molar percent yield) of dimethyl ether. Certain embodiments of the processes are carried out in a system comprising multiple microchannel reactors.

Also disclosed are processes for producing dimethyl ether comprising providing a source of syngas, providing a hybrid catalyst, reacting the syngas and the hybrid catalyst at a temperature from about 200° C. to about 400° C. with a contact time of from about 25 milliseconds to less than about 500 milliseconds, and producing greater than about 60% conversion of CO to dimethyl ether. Certain embodiments of the processes are carried out in reactors providing greater surface to volume ratios than the presently used DME reactors. Certain embodiments of the processes are carried out in systems comprising multiple microchannel reactors.

Also disclosed are systems for producing DME from methanol wherein the system includes a module including a plurality of microchannel reactors, a source that feeds methanol to a methanol dehydration catalyst, or a plurality of microchannel reactors and a source that feeds syngas to a hybrid catalyst, and wherein the microchannel reactors are operable at temperatures of greater than about 250° C. and with a contact time of less than about 250 milliseconds to produce a DME yield of greater than about 70% (molar percent yield when referring to DME production from methanol and percent conversion of CO to DME when referring to DME from syngas). An alternative application includes on-demand synthesis of DME from either syngas or methanol The foregoing and other objects, features, and advantages of the invention will become more apparent from the following detailed description, which proceeds with reference to the accompanying figures.

DETAILED DESCRIPTION

Figure 1:
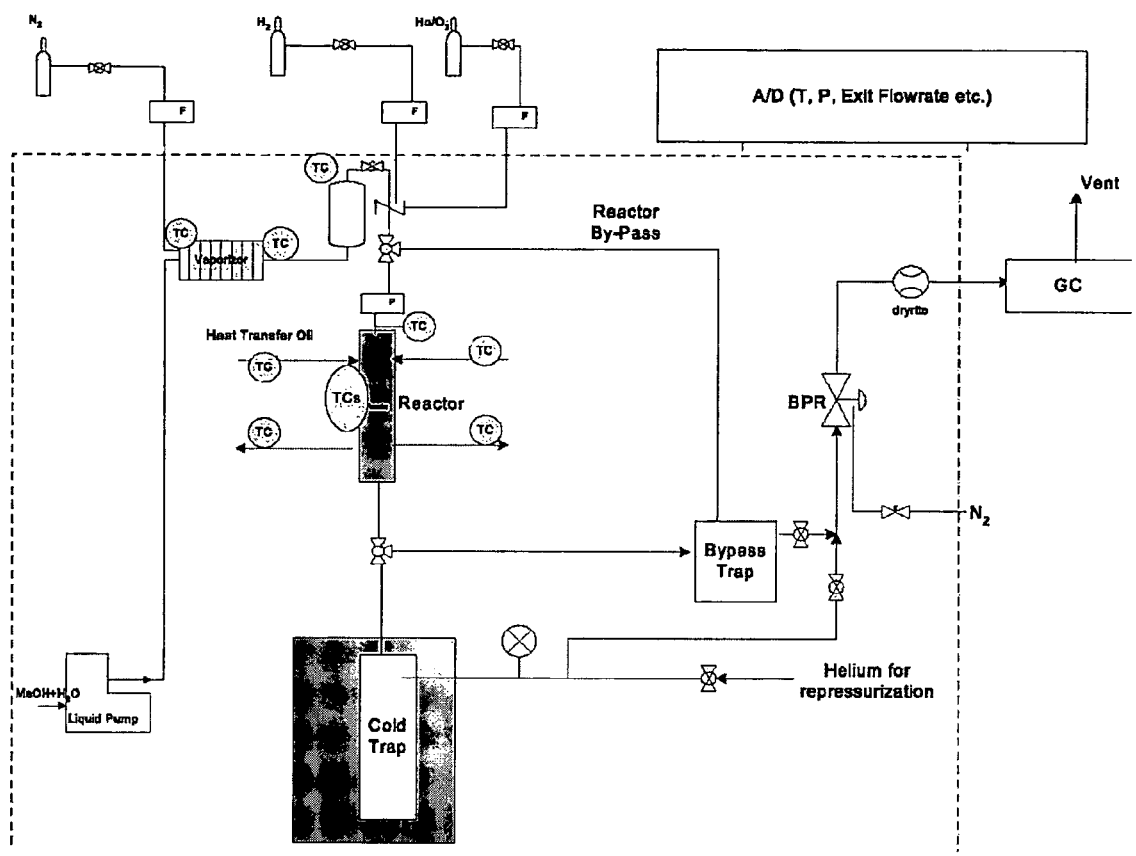
FIG. 1 is a schematic diagram of a reactor system and microchannel reactor assembly that may comprise certain embodiments of the disclosed invention.

Disclosed are methods for producing dimethyl ether (DME) from methanol and for producing DME directly from syngas, such as syngas from biomass. Also disclosed are apparatus for DME production.

As used herein, the singular terms "a," "an," and "the" include plural referents unless context clearly indicates otherwise. The word "comprises" indicates "includes." It is further to be understood that all molecular weight or molecular mass values given for compounds are approximate, and are provided for description. In addition, all physical parameters, such as temperatures, pressures and amounts are approximate unless otherwise indicated, whether the parameter is preceded by the word "about" or is not. The materials, methods, and examples are illustrative only and not intended to be limiting. Unless otherwise indicated, description of components in chemical nomenclature refers to the components at the time of addition to any combination specified in the description, but does not necessarily preclude chemical interactions among the components of a mixture once mixed. As used herein percent (%) or percent yield refers to molar percent yield when referring to DME production from methanol. Percent (%) values when referring to DME produced from syngas refers to percent conversion of CO to DME.

DME may be produced via a methanol dehydration reaction, using acidic catalysts, such as phosphoric-acid modified gamma Al$_2$O$_3$, in a fixed-bed reactor. The cost of producing DME from methanol is influenced by price and availability, as methanol itself is an expensive chemical feedstock. Producing DME directly from syngas has many economic and technical advantages over methanol dehydration. Thermodynamically, DME production from syngas is more favorable than from methanol, and the cost for DME production from syngas is lower with use of a suitable catalyst.

Direct DME synthesis involves many competing reaction pathways:

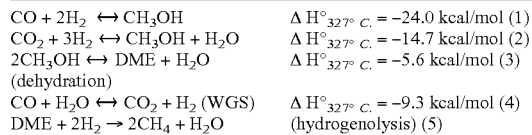

| | |
|---|---|
| CO + 2H$_2$ ↔ CH$_3$OH | Δ H°$_{327°\,C.}$ = −24.0 kcal/mol (1) |
| CO$_2$ + 3H$_2$ ↔ CH$_3$OH + H$_2$O | Δ H°$_{327°\,C.}$ = −14.7 kcal/mol (2) |
| 2CH$_3$OH ↔ DME + H$_2$O (dehydration) | Δ H°$_{327°\,C.}$ = −5.6 kcal/mol (3) |
| CO + H$_2$O ↔ CO$_2$ + H$_2$ (WGS) | Δ H°$_{327°\,C.}$ = −9.3 kcal/mol (4) |
| DME + 2H$_2$ → 2CH$_4$ + H$_2$O | (hydrogenolysis) (5) |

DME from Methanol

Certain embodiments of the disclosed methods and apparatus comprise forming DME from methanol using a methanol dehydration reaction. In particular embodiments, the process parameters of temperature, contact time and catalyst produce a DME yield (molar percent yield) of greater about 70% or about 80% or even about 90%. In various embodiments of the disclosed methods suitable catalysts are used in conjunction with contact times as low as about 15 milliseconds and at temperatures as high as greater than about 500° C., at pressures of from about 1 atm to about 40 atm or at pressures of less than about 9 atm.

Catalysts for DME from Methanol

Certain embodiments of the disclosed methods include use of a zeolite catalyst with a Si/Al ratio of 12, 30, 60, or 80. A particularly suitable catalyst comprises H-ZSM-5 zeolite with a Si/Al ratio of 30. A suitable catalyst for producing DME from MeOH may include acidic catalysts, γ-aluminas, and palladium-doped γ-aluminas. Palladium-doped γ-alumina catalysts may be doped at a variety of concentrations, for example from about 0.1 to about 20%, such as 0.5, 1, 2, or 13%, by weight. Other suitable catalysts for producing DME from MeOH may include, e.g., zeolites with various Si/Al ratios (e.g., H-ZSM-5 available from Zeolyst International) or the zeolite mordenite, phosphoric-acid modified aluminas, titanates, tungsten oxide, supported heteropoly acid catalysts preferably with controlled acidities, or, e.g., titania or titania modified alumina or zirconia. Heteropoly acid catalysts may have controlled acidities by treatments known to those of ordinary skill in the art such as shown, for example, in Nakato, et al., "Changes of Surface Properties and Water-Tolerant Catalytic Activity of Solid Acid Cs2.5H0.5PW12O40", Langmuir, 14, 319-325 (1998), which is incorporated herein by reference.

Gas Hourly Space Velocity or Contact Time for DME from Methanol

In particular embodiments the gas hourly space velocity through the reaction zone ranges from about 240000 h$^{-1}$ to about 3600 h$^{-1}$, preferably from about 240000 h$^{-1}$ to about 72,000 h$^{-1}$. The gas hourly space velocity is defined as the volume of reactants per time per reaction zone volume. The volume of reactant gases is at standard conditions of pressure (1 atm or 101 kPa) and temperature (0° C. or 273.16 K). The reaction zone volume is defined by the portion of the reaction vessel volume where reaction takes place and which is occupied by a gaseous phase comprising reactants, products, and/or inerts; a liquid phase comprising aqueous and/or organic phases; and a solid phase comprising catalyst. Gas hourly space velocity is the inverse of contact time, and thus, this process parameter may also be characterized in terms of contact time rather than gas hourly space velocity. Suitable contact times may be from about 15 to about 250 milliseconds or from about 15 to about 50 milliseconds or from about 15 to about 100 milliseconds or less than about 150 milliseconds, preferably less than about 50 milliseconds. Conventional methods use much longer contact times as compared to the short contact times used in the disclosed embodiments; shorter contact times were likely not used to date for producing DME due to the relatively poor heat transfer in conventional reactors with which such short contact times would have resulted in low DME yields.

Although contact times are set forth above for a number of embodiments of the disclosed methods, preferred contact times will depend in part on the catalyst chosen and other process parameters (e.g., the process temperature and the type of reactor utilized for the reaction), as would be understood by one of ordinary skill in the art. It is to be understood that other "short" contact times may be suitable for a particular catalyst—any given catalyst requires sufficient "contact time" for the reaction of methanol-to-DME to occur. However, if too much contact time occurs (if the contact time is too high), undesired reactions occur resulting in unwanted byproducts instead of DME. Certain embodiments of the disclosed methods utilize short contact times in part due to operation of the disclosed methods in microchannel devices which provide relatively high surface to volume ratios as compared to conventional reactors.

Process Temperatures for DME from Methanol

The embodiments of the disclosed methods operate at temperatures much higher than conventionally used to produce DME. The methods as disclosed herein benefit from carrying out the processes in microchannel devices so as to allow the process to operate at substantially or near isothermal conditions. Conventional reactors for DME production have not provided the benefit of isothermal or near isothermal reaction environments. Fast kinetics (high turnover rates achievable at relatively short contact times) and isothermal conditions (temperature control) favor the DME production. In certain embodiments of the disclosed methods the reaction zone temperature is typically in the range of from about 200° C. to 500° C. Preferably, the reaction zone is operated at temperatures of from about 250° C. to 350° C., or at temperatures of about 300° C.

Figure 3A:
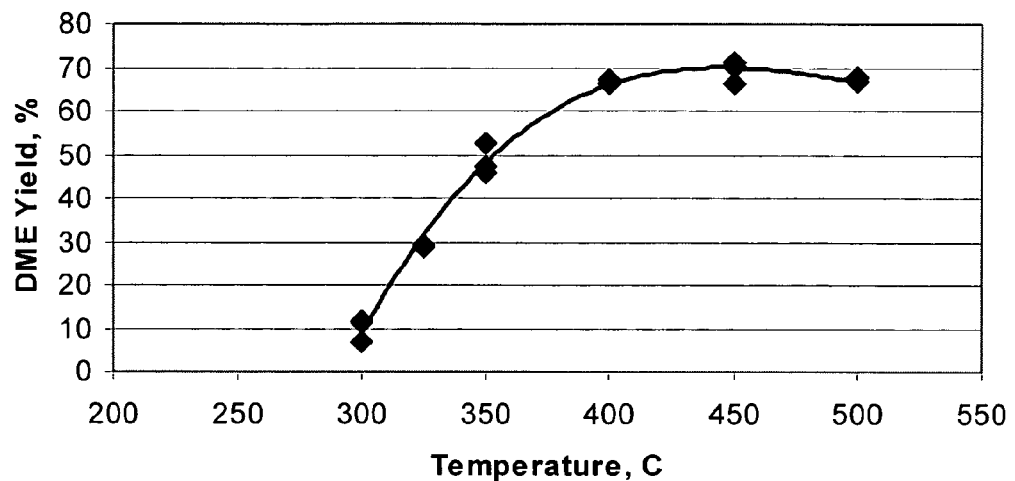
FIG. 3a illustrates DME yields in certain embodiments of the disclosed process for producing DME from methanol.

As can be seen by reference to FIG. 3a, a DME yield of about 70% was obtained when using a γ-alumina catalyst (a γ-alumina catalyst with no additives, purchased from Engelhard) at a temperature of 450° C. with a contact time of about 100 milliseconds and about an 80% methanol feed.

Figure 3B:
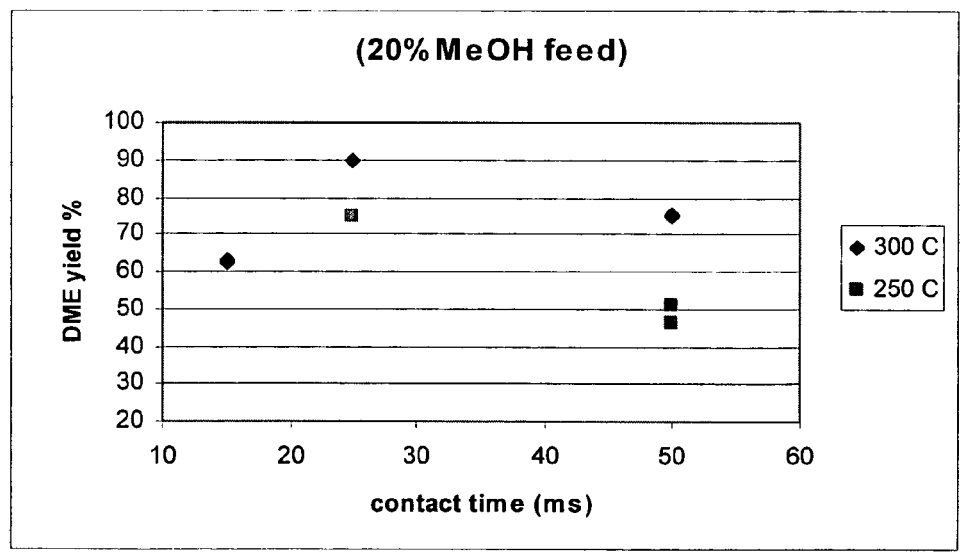
FIG. 3b illustrates DME yields in certain embodiments of the disclosed process for producing DME from methanol.

As shown in FIG. 3b, a DME yield of about 90% was achieved at a contact time of about 25 milliseconds with zeolite catalyst having a Si/Al ratio of 30 was used and the process took place at about 300° C. with a 20% methanol feed. A DME yield of about 75% was achieved at a contact time of about 25 milliseconds when zeolite catalyst having a Si/Al ratio of 30 was used and the process took place at about 250° C. with a 20% methanol feed. At a contact time of 50 milliseconds, a DME yield of about 75% was achieved when zeolite catalyst having a Si/Al ratio of 30 was used and the process took place at about 300° C. with a 20% methanol feed.

Figure 4A:
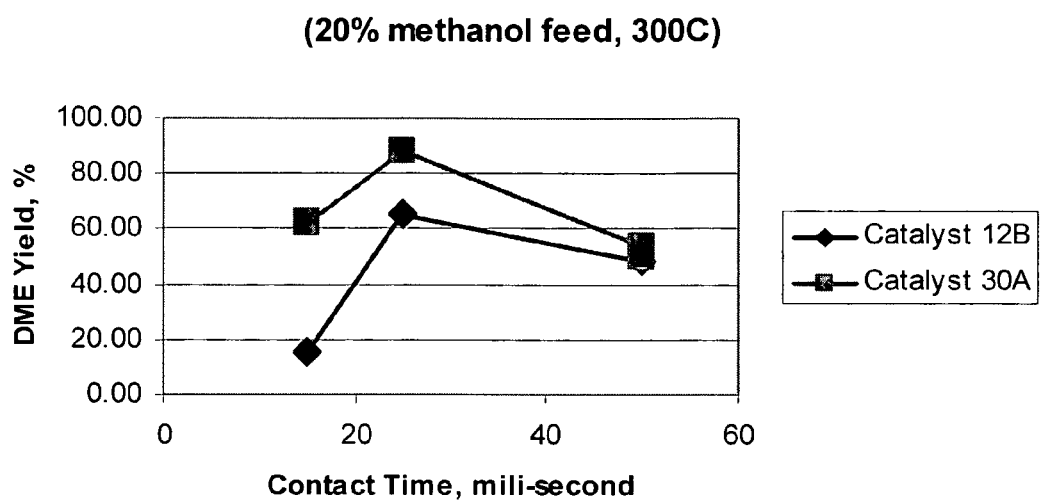
FIG. 4a illustrates DME yields in certain embodiments of the disclosed process for producing DME from methanol.
Figure 4B:
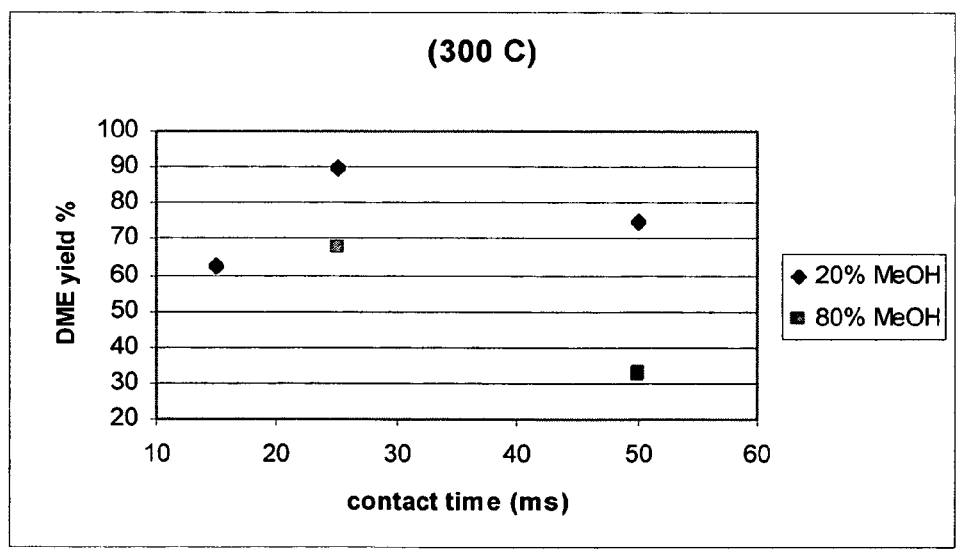
FIG. 4b illustrates DME yields in certain embodiments of the disclosed process for producing DME from methanol.

As can be seen with reference to FIG. 4a, when using catalyst 12B or 30A (12B is a Si/Al=12 zeolite and 30A is a Si/Al=30 zeolite, both available from Zeolyst International) at about 300° C. with a 20% methanol feed with contact times varying from about 15 to about 50 milliseconds, good DME yields were generally achieved, especially at contact times of about 25 milliseconds. As shown in FIG. 4b, a DME yield of about 90% was achieved at a contact time of about 25 milliseconds when zeolite catalyst having a Si/Al ratio of 30 was used and the process took place at about 300° C. with a 20% methanol feed. Although higher temperatures (i.e., 275° C.-420° C.) have been reported as used in conventional DME production methods, such higher temperatures had to be used in conjunction with relatively high pressures (i.e., from 1000 kPa-1700 kPa (~10-15 atm)).

Process Pressures for DME from Methanol

For particular embodiments of the disclosed methods for producing DME from methanol, the reaction zone pressure is typically at atmospheric pressure but the pressure could be varied to be in the range of about 1 atm to about 10 atm.

DME from Syngas

Another embodiment of the disclosed methods comprises forming DME from syngas using a hybrid catalyst system. The syngas useful for performing the disclosed methods includes any suitable syngas source, such as syngas from biomass, coal, and/or natural gas. A hybrid catalyst system including methanol synthesis from syngas and methanol dehydration catalysts are used to directly produce DME. Suitable catalyst hybrids are used in conjunction with relatively short contact times and at relatively high temperatures.

Catalysts for DME from Syngas

Certain embodiments of the disclosed methods include use of the following catalysts: a combination of a methanol synthesis catalysts (e.g., copper-based or palladium-based synthesis catalysts) such as F51-8PPT (available from Kataco Corp., formerly ICI India Ltd.), and dehydration catalysts, ZSM-5 zeolite with a Si/Al ratio of 30 (available from Zeolyst International) and acidic $Al_2O_3$ (available from Engelhard Corp.), solid acid $Al_2O_3$ containing 4 wt % fluoride (F—$Al_2O_3$ available from Engelhard).

TABLE 1

Dehydration Activity of Solid Acid Catalysts under DME Synthesis Conditions (Pressure 3.8 MPa, Temperature 280 q° C.)

| CATALYSTS | ZSM-5 | F-AL2O3 | ACIDIC AL2O3 | USY-ZEOLITE |
|---|---|---|---|---|
| conversion | 80.0 | 79.3 | 79.7 | no dehydration activity |
| selectivity | | | | |
| DME | 60.2 | 63.4 | 62.7 | |
| MeOH | 10.3 | 10.2 | 7.4 | |
| CO2 | 27.0 | 22.7 | 22.3 | |
| $CH_4$ | 2.5 | 3.7 | 7.6 | |
| $C_2^+$ Oxy | | | | |
| total | 100 | 100 | 100 | |

Certain useful dehydration catalysts for performing particular embodiments of the disclosed methods are shown in Table 1. Although the acid strengths of these catalysts are different, $Al_2O_3$, F—$Al_2O_3$, and ZSM-5 yield the same conversion and selectivity. The USY zeolite (ultra stable Y-zeolite) exhibits the lowest dehydration activity. A CO conversion of about 40% is obtained, which is the same as methanol-only synthesis. Low DME selectivity (10%) further confirms that the loss of dehydration activity is responsible for low CO conversion as discussed below. Without being tied to any particular theory, it is believed that the unexpected phenomenon might be associated with the blocking of acid sites by water. Y-zeolite contains less acid sites but higher acid strength than H-ZSM-5. It is plausible that water produced from the reaction strongly adsorbed on acid sites, therefore inhibiting the dehydration reaction rate. Thus, direct DME synthesis does not require strong solid acid and the acidity (number of acid sites) of the dehydration catalyst is more important than the acid strength.

Figure 13:
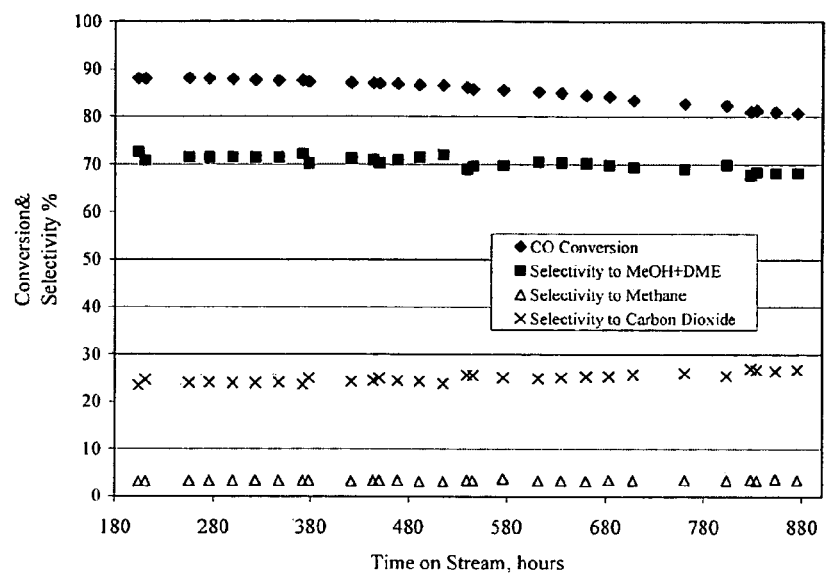
FIG. 13 illustrates direct syngas conversion to DME in certain embodiments disclosed herein (with a mixture of methanol synthesis catalyst and H-ZSM-5; P=3.8 MPa, GHSV=5000 h$^{-1}$, H$_2$/CO=3, T=280° C.).

The hybrid catalyst system used in certain embodiments disclosed herein include DME synthesis performed under conditions of 280° C., 3.8 MPa and GHSV of 5000 h-1. It has been found that stability of the catalysts is affected by the presence of water. One particular embodiment comprises a hybrid catalyst system combining commercial methanol synthesis catalysts and a ZSM-5 zeolite. As shown in FIG. 13, initial CO conversion of about 88% is obtained. As the process proceeds a slow decrease in CO conversion is produced. Throughout the process in this embodiment, selectivity to $CO_2$ increases slightly, but methane selectivity remains unchanged. From a carbon utilization point of view, the formation of $CO_2$ from the water-gas shift (WGS) reaction appears to have negative effect on DME yield. However, the WGS reaction is preferred in DME synthesis to keep water concentration low, so as to enhance the rate of the dehydration reaction. This is especially useful for a CO-rich feedstock, as the WGS reaction can also balance the ratio of CO and $H_2$ by depleting CO and forming $H_2$.

It has been reported that the presence of water inhibits dehydration activity. However, as disclosed in certain methods herein, with the use of the disclosed hybrid catalyst, deactivation is not significant. Excess water, upon formation in the reaction, may be removed via the WGS reaction. The WGS reaction proceeds at faster reaction rates than as conventionally believed and reach equilibrium to yield 22% $CO_2$. The WGS reaction depletes the water produced from the dehydration reaction, which may reduce the interaction between water and methanol catalyst, and therefore retard catalyst sintering.

In certain embodiments, the catalysts are pre-treated in manners known to those of ordinary skill in the art to improve performance. For example, the dehydration catalysts may be calcined in air at high temperatures (e.g., 500° C.) to remove physically absorbed moisture for both the MeOH synthesis and dehydration catalysts may be crushed and sieved (e.g., sieved into 70-100 mesh).

Figure 9:
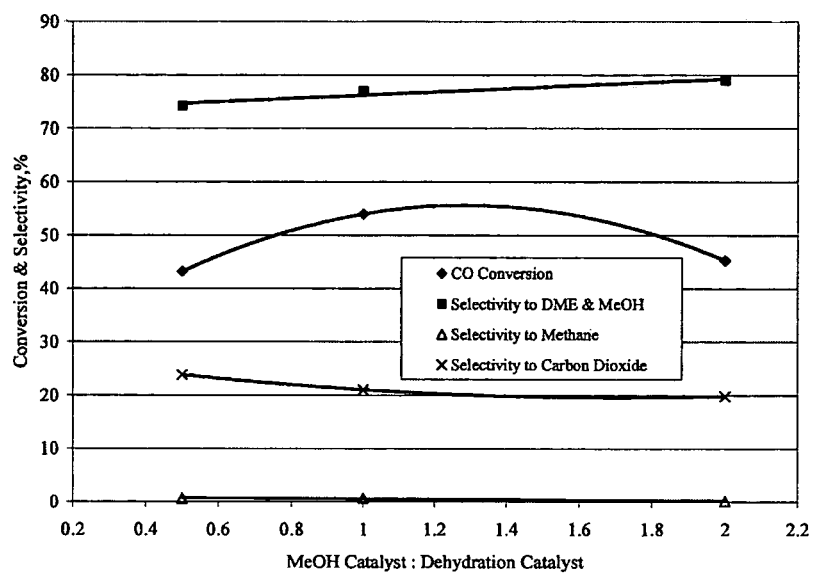
FIG. 9 illustrates the effect of catalyst ratio on CO conversion in certain embodiments disclosed herein (MeOH synthesis catalyst: dehydration catalyst; T=260° C., P=3.8 MPa, $H_2/CO=3$, GHSV=10 000 $h^{-1}$).

The hybrid catalyst may be prepared by mixing the synthesis and dehydration catalysts in any suitable fashion, such as by mechanically mixing the catalysts at a desired ratio. It has been discovered that an important parameter in the design of such a hybrid or dual catalyst system is the catalyst loading ratio, that is, the methanol dehydration to methanol formation activity. Too high of a methanol dehydration activity compared with WGS activity leads to a high water production. Results shown in FIG. 9 indicate that CO conversion is affected by the catalyst ratio, but product selectivity is not sensitive to the change of catalyst ratio. A particularly useful catalyst ratio appears to be about 1:1 by weight but other ratios, such as 2:1 may be used. Conventionally, ratios of about 4:1 and higher are used; although such ratios may be used in certain embodiments of the disclosed methods, lower ratios provide greater DME yields.

Gas Hourly Space Velocity or Contact Time for DME from Syngas

In particular embodiments the gas hourly space velocity through the reaction zone ranges from about 500 $h^{-1}$ to about 100,000 $h^{-1}$, preferably from about 3,600 $h^{-1}$ to about 36,000 $h^{-1}$. The gas hourly space velocity is defined as the volume of reactants per time per reaction zone volume. The volume of reactant gases is at standard conditions of pressure (1 atm or 101 kPa) and temperature (0° C. or 273.16 K). The reaction zone volume is defined by the portion of the reaction vessel volume where reaction takes place and which is occupied by a gaseous phase comprising reactants, products, and/or inerts; a liquid phase comprising liquid products and/or other liquids; and a solid phase comprising catalyst.

Put another way, suitable contact times for production of DME directly from syngas may be from about from about 0.025 s to about 7.2 s, or from about from about 0.036 s to about 7.2 s less than about 1 s, or less than about 0.5 s. Conventional methods use much longer contact times than the short contact times used in the disclosed embodiments; shorter contact times were likely not used due to the relatively poorer heat transfer in conventional reactors, which severely limit syngas conversion and selectivity at short contact times.

Figure 7:
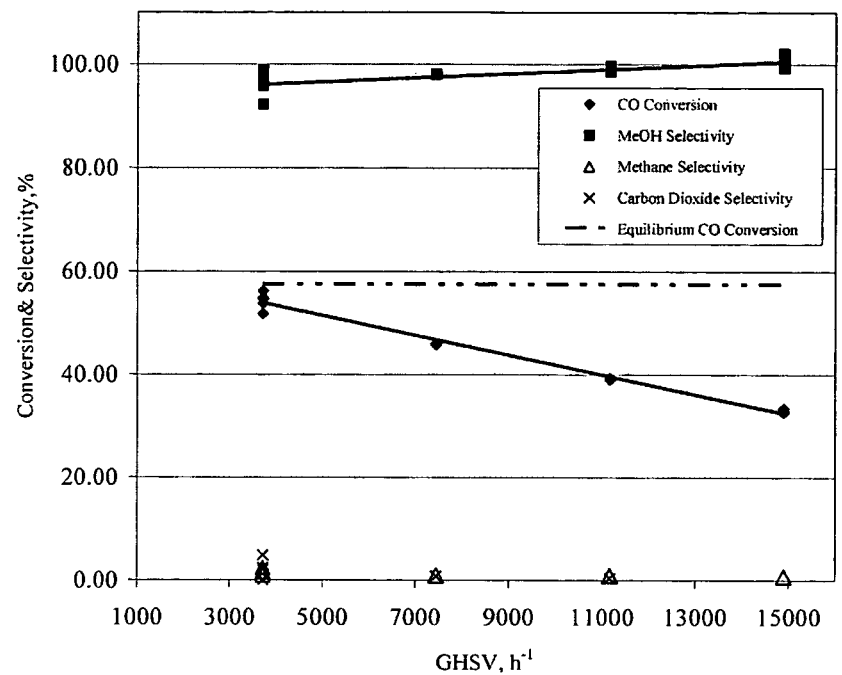
FIG. 7 illustrates the effect of GHSV on methanol synthesis in certain embodiments disclosed herein.
Figure 12:
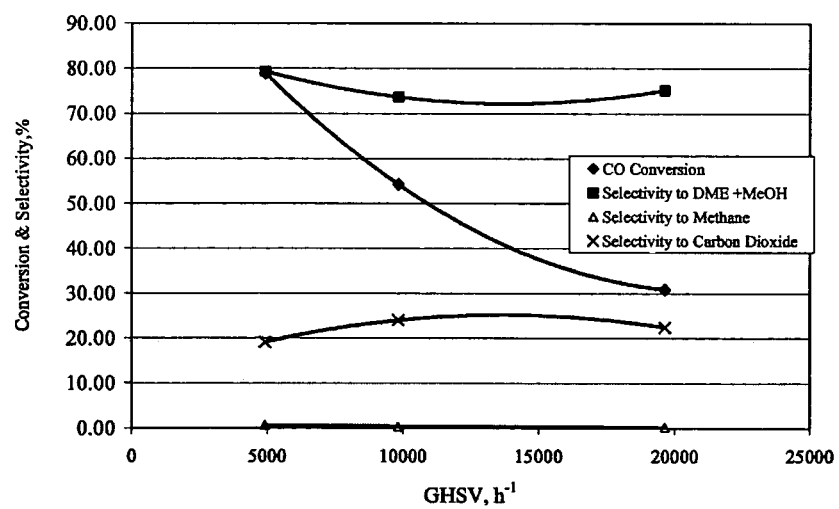
FIG. 12 illustrates the effect of GHSV on syngas conversion to DME in certain embodiments disclosed herein (mixture of methanol synthesis catalyst and H-ZSM-5; P=3.8 MPa, H$_2$/CO=2, T=286° C.).

As shown in FIG. 7, methanol synthesis is conducted under constant temperature of about 250° C. and pressure of about 3.8 MPa. When using decreasing GHSV, CO conversion increases first and begins to approach equilibrium conversion of about 50%. This response may be in large part occur because methanol synthesis is thermodynamically limited. In contrast, as shown in FIG. 12, in one particular embodiment of direct DME synthesis, conversion increases significantly with a decrease in GHSV. When GHSV is decreased from 20,000 to 5,000 $h^{-1}$, conversion is increased from 31% to 80%. Even when GHSV is changed, selectivity to $CO_2$ remains fairly stable.

Process Temperatures for DME from Syngas

The embodiments of the disclosed methods operate at temperatures much higher than conventionally used to produce DME. The ability to carry out the process of these embodiments at relatively high temperatures is due at least in part to the use of microtech-sized reactors as described further below, and the ability to carry-out the reactions in a substantially isothermic environment. In certain embodiments of the disclosed methods the reaction zone temperature is typically in the range of from about 200° C. to about 400° C. or from about 200° C. to about 350° C. Preferably, the reaction zone is operated at temperatures of from about 240° C. to about 290° C.

Figure 10:
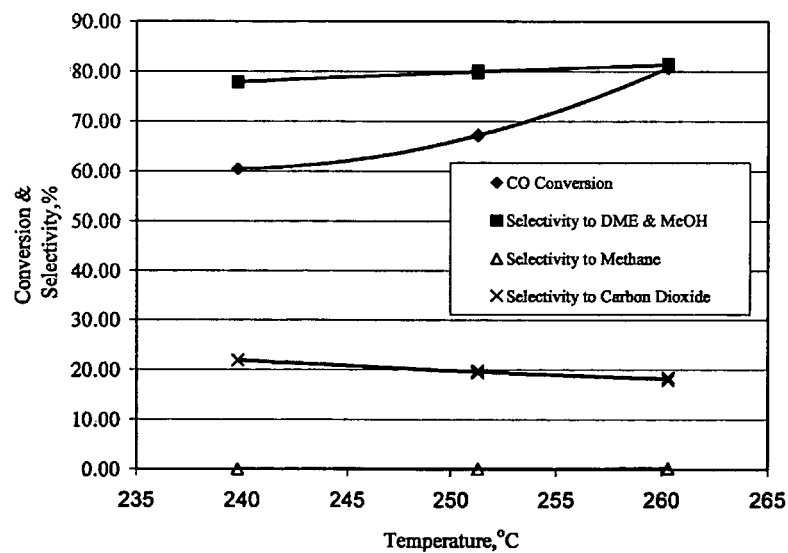
FIG. 10 illustrates the effect of reaction temperature on syngas conversion to DME in certain embodiments disclosed herein (mixture of methanol synthesis catalyst and H-ZSM-5; P=3.8 MPa, GHSV=5000 h$^{-1}$, H$_2$/CO=3).

In one embodiment, a temperature range of from about 240° C. to about 260° C. is used and the effect of the temperature on the catalytic activity of a methanol synthesis catalyst and ZSM-5 catalyst combined is depicted in FIG. 10. In this particular embodiment a microchannel reactor sun as shown in FIG. 1 is operated in an isothermal mode. Two thermal couples are installed in a catalyst bed and a furnace temperature is used to control the catalyst bed temperature. The temperature difference between the top and bottom catalyst bed may be controlled within about 2° C., indicating excellent heat removal capability of the microchannel reactor. Unlike methanol synthesis alone, where CO conversion decreases with an increase in reaction temperature, FIG. 10 shows that temperature has a positive effect on CO conversion in direct syngas conversion to DME. The embodiments utilizing microchannel reactors can be operated at higher reaction temperatures (and lower pressures) than are conventional reactors to achieve high space time yield but can still operate in the isothermal regime. At a GHSV of 5000 $h^{-1}$, CO conversion of about 80% is achieved but is below the equilibrium limit of DME synthesis (94%). Thus the dehydration reaction may proceed at slower rate than the methanol synthesis reaction and only a relatively low GHSV is needed to approach equilibrium conversion.

A large amount of $CO_2$ may be produced via the WGS reaction. Within the operating temperature range disclosed for these embodiments selectivity to $CO_2$ remains substantially constant. As a result of isothermal operation in microchannel reactors, hot spots on the catalyst surface and between catalyst particles are eliminated; therefore, negative side reactions are not favored.

Process Pressures for DME from Syngas

The reaction zone pressure is typically in the range of about 0.5 MPa to about 40 MPa, more preferably from about 1 MPa to about 12 MPa, and still more preferably from about 2 MPa to about 8 MPa.

Figure 11:
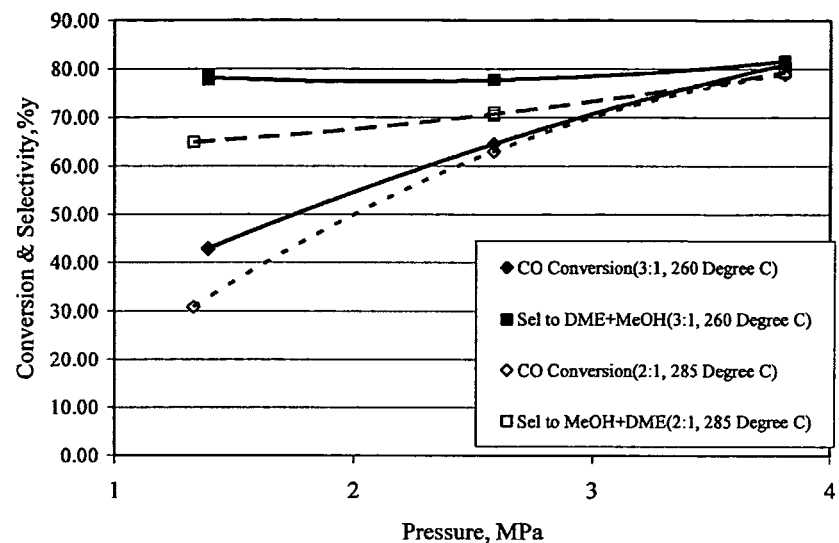
FIG. 11 illustrates the effect of pressure and H2/CO ratio on DME formation in certain embodiments disclosed herein (mixture of methanol synthesis catalyst and H-ZSM-5; GHSV=5000 h$^{-1}$).

In certain embodiments, processes are utilized (with a GHSV of about 5000 $h^{-1}$), using different feed compositions ($H_2$/CO) 3:1 and 2:1. Increasing the pressure exhibited a positive effect on DME formation. As shown in FIG. 11, at a relatively low pressure of about 1.0 MPa, low CO conversion occurs. A sharp increase in CO conversion is observed when pressure is increased from about 1.0 to about 3.8 MPa. This counters conventional belief where it is indicated that in DME synthesis CO conversion increases with increased pressure but levels off at 2 MPa, beyond which the impact of pressure on CO conversion was not significant. Without being tied to any particular theory, it is proposed that using syngas as a raw fuel source, and perhaps utilizing a microtech reactors configuration, and because the use of two functionally independent catalysts are closely interrelated, the performance of DME synthesis in, e.g., a microchannel reactor is different from conventional fixed-bed or slurry reactors allowing for greater DME yield at higher pressures.

One embodiment for producing DME includes conversion of DME from methanol or DME from syngas in a microtech system, such as microchannel reactor. Suitable microtech systems are described in, e.g., U.S. Pat. No. 6,616,909, which is incorporated herein by reference. Microchannel reactors have the advantage of improved heat and mass transfer, having larger surface to volume ratios than do conventional reactors, which allow for greater process intensification. Air Products commercial demonstration results obtained from a slurry reactor were compared with the hybrid catalyst/microchannel reactor system as disclosed herein. The performance results are shown in Table 2.

TABLE 2

Performance Comparison of Syngas Conversion to DME in Different Reactor Configurations

| reactor configurations reaction conditions | Air Products slurry | microchannel |
|---|---|---|
| T, °C. | 250 | 280 |
| P, atm | 52 | 38 |
| GHSV, h$^{-1}$ | 4500 | 10 238 |
| H$_2$/CO | 0.7 | 2 |
| performance conversion | 37 | 80 |
| CO$_2$ selectivity | 32 | 22 |
| specific activity, gCO/g · h | 1.19 | 3.52 |
| liquid yield, g/(g, h) | 0.79 | 2.25 |

Figure 2:
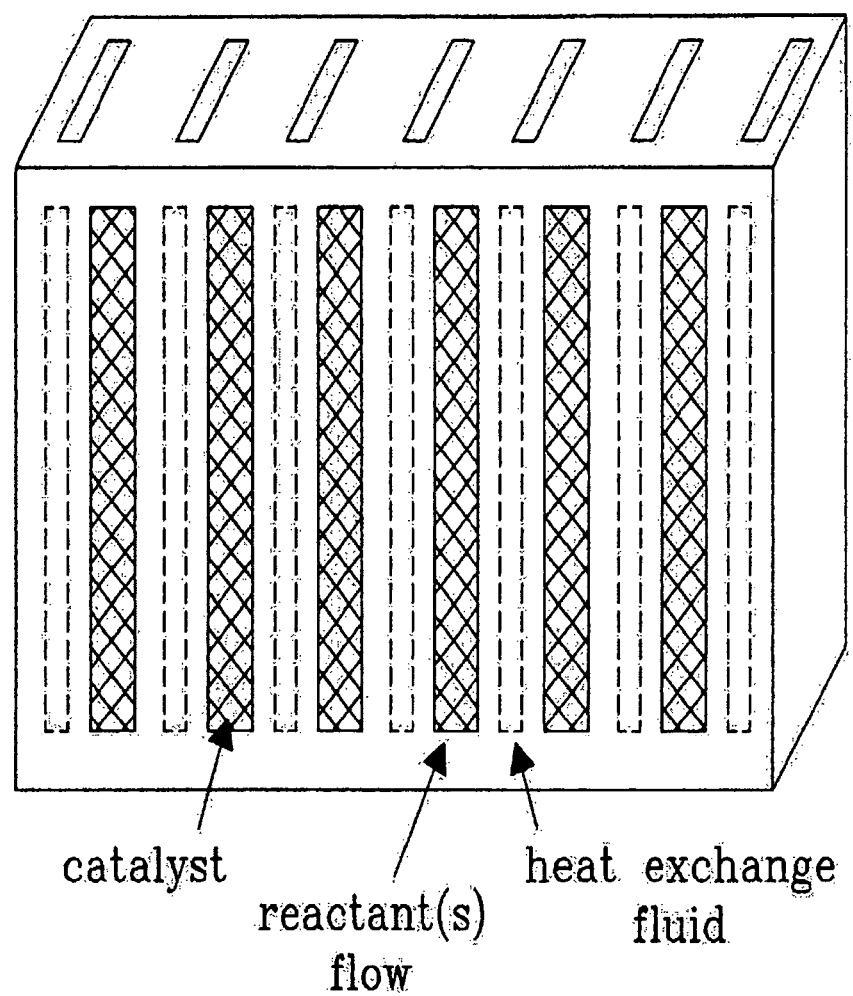
FIG. 2 illustrates an embodiment of a microchannel device.

By way of example in FIG. 2, a possible embodiment of a microchannel device is shown. The distance from the heat source to heat sink is about 1 centimeter or less. This distance is a function of the heat duty, the selection of heat transfer fluid(s), and the effective thermal conductivity of a porous catalyst insert. Thin sheets or tubes can be used to obtain high heat duties and short contact times. The thickness of the web between the reaction channel and the heat exchange channel can vary, but is preferably between about 0.01 inches and about 0.25 inches. The preferred thickness for the heat exchange channel preferably ranges from 100 microns to 10 millimeters. The preferred thickness is 250 microns to 3 millimeter. Flow of the heat transfer fluid may be either counter-current, cross-current, or co-current to the direction of the flow of reactants.

A microchannel reactor is preferably able to operate at relatively severe conditions to obtain high productivity. As shown in Table 2, DME synthesis may be conducted in a microchannel reactor at GHSV=10 238 h$^{-1}$, 2.2 times higher than in the commercial slurry reactors. Side-by-side comparison reveals excellent performance of microchannel reactors. A specific activity of 3.52 g of CO/(g,h) and a space time yield of 2.25 g/(g,h) are obtained, respectively. Even when the microchannel reactor was operated under severe conditions, selectivity to byproducts produced from methanation and pyrolysis were negligible. It is generally believed that back mixing occurs in the conventional slurry reactor, which affects product selectivity, resulting in much lower DME yields than the presently disclosed methods. Back mixing was not present in the microchannel reactor.

Enhancement in space time yield is also attributed to improved mass transfer in a microchannel reactor. Compared with the conventional fixed-bed reactors, the (bulk) diffusion length from gas phase to catalyst surface is significantly reduced. Furthermore, unlike the slurry reactors, there is no liquid holdup inside the microchannel reactor. Calculations show that in the microchannel reactor under reaction conditions, the internal diffusion limitation is significantly reduced. In addition, a high linear velocity in the microchannel reactors facilitating the removal of water from the catalyst surface, releasing blocked acid sites and accelerating the dehydration reaction.

A microchannel reactor is effective for achieving high productivity in direct DME synthesis. The performance of the hybrid bifunctionalized catalyst system is much higher than that in conventional reactors, as a result of improved heat and mass transfer. Heat transfer improvement eliminates hot spots, which improves catalyst stability and product selectivity. The improved mass transfer capability of a microchannel reactor is attributable to the shortening of bulk diffusion length, minimizing back-mixing and increasing accessibility from the gas phase to the catalyst surface, which leads to an enhanced space time yield.

Figure 14:
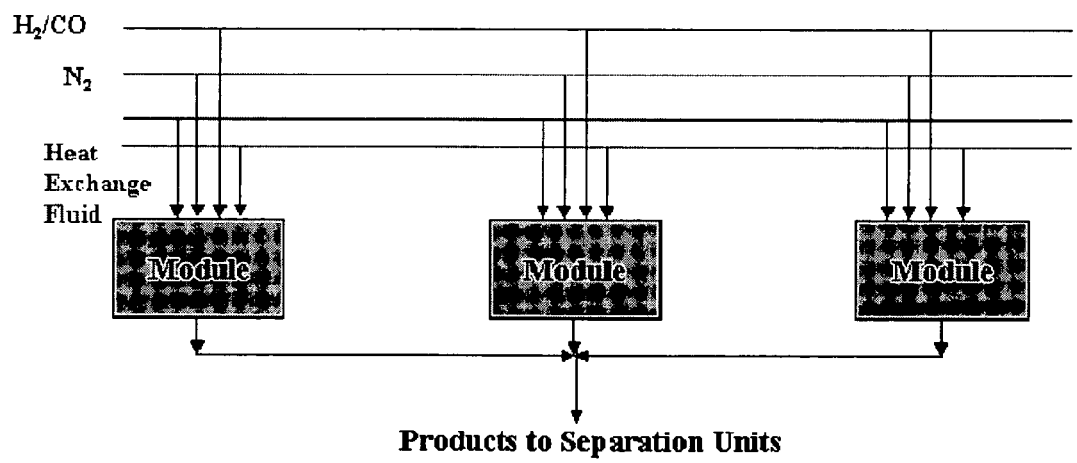
FIG. 14 illustrates one possible embodiment of a modular design of commercial DME production plant utilizing microchannel reactors.

One embodiment of a commercial scale plant design based on use of microchannel reactors is shown in FIG. 14. Utilizing microchannel technology intensifies the process by a factor of about 40 to about 1000 as compared to conventional reactor technology and DME production processes.

A module suitably sized to accommodate the desired productivity and operational flexibility may contain many hundreds of micro-channels. An estimation of the number of potential modules and their sizes based on a production capacity of 120,000 tons/yr of DME are summarized in Table 3. The system capacity can be adjusted by changing the number of modules. As illustrated in the embodiment shown in FIG. 14, a commercial DME production system may operate utilizing microchannel modular devices. The total volume occupied by these modules is approximately 1500 to about 2000 L. The disclosed embodiments of commercial-sized DME production systems are about 300 times smaller than would be a conventional commercial scale reactor system for converting syngas to DME reactor to achieve the same productivity as achieved by the disclosed methods and apparatus.

In general, as used herein, a microtech or microchannel device refers to a reactor wherein the reaction chamber has a cross-section of less than about 5 mm. Certain embodiments of the disclosed commercial-scale microtech or microchannel systems may comprise, for example, from about 100 to about 300 modular reactors (modules) wherein the individual modules include at least about 100 microchannels. As used herein, commercial-scale microtech or microchannel system means a system having at least about 50 reactor modules with the modules having at least about 50 to about 100 microchannel reactors. A characteristic or feature of the microtech devices as disclosed herein is the ability of such devices to operate during the DME production process in a substantially isothermal environment. Put another way, the microtech devices utilized with certain embodiments of the disclosed processes are devices capable of operating substantially isothermally when producing DME due to the devices' heat transfer abilities. Thus, an advantage of using the disclosed microchannel reactors for the exothermic DME synthesis reaction is that reactor temperature is uniformly distributed in the reactor.

TABLE 3

Embodiment of a DME Synthesis Plant Utilizing Microchannel Modules

| | |
|---|---|
| Plant Capacity, tons/yr | 120,000 |
| GHSV, $h^{-1}$ | 100,000 |
| Syngas single pass conversion, % | 50-90 |
| Total modules | 100-300 |
| Estimated physical volume of each module(total), liters | 7.2 |
| Number of channels in a module | 100-600 |

EXAMPLES

A hybrid catalyst system, including methanol synthesis and dehydration catalysts, was developed to test direct synthesis of biomass syngas to produce DME. The experiments were carried out in a microchannel reactor (316 stainless steel), with the dimensions 5.08 cm×0.94 cm×0.15 cm. Three commercial catalysts were used: a methanol synthesis catalyst, F51-8PPT (Kataco Corp.); and two dehydration catalysts, ZSM-5 zeolite with a Si/Al ratio of 30 (Zeolyst International) and acidic Al2O3 (Engelhard Corp.). Solid acid $Al_2O_3$ containing 4 wt % fluoride was also used as dehydration catalyst (F—$Al_2O_3$) Prior to reaction, the zeolite and acidic catalysts were calcined in air at 500° C. to remove physically absorbed moisture. Both the methanol synthesis catalyst and the dehydration catalyst were crushed and sieved into 70-100 mesh. The hybrid catalyst was prepared by mechanically mixing the two types of catalysts in a transparent vial at a desired ratio and charged in the microchannel reactor. This is high pressure down flow fixed-bed type of reactor. The schematic diagram of the reactor system and microchannel reactor assembly were as shown in FIG. 1.

To minimize methanation reaction in the stainless steel reactor, silicone-coated stainless steel tubing was used in the high-temperature preheating zone. Experiments were conducted at temperatures from 220 to 320° C. and pressure from 2 to 5 MPa. All the experiments were carried out under isothermal conditions as indicated by the uniform temperature distribution along catalyst bed. The hybrid catalyst (mixture of methanol synthesis and ZSM-5) was reduced with 10% hydrogen in helium in the 220-350° C. temperature range at atmospheric pressure. A mixture of $N_2/H_2$ was fed during startup to establish steady-state flow and to heat the reactor to the desired temperature. When the catalyst bed temperature reached the target, premixed syngas at the desired ratio was fed into the reactor.

The typical feed composition was CO:$H_2$:$CO_2$:Ar=30:62:4:4. The presence of Ar served as the internal standard for conversion and selectivity calculation purposes. Total feed flow rate was set to achieve the desired gas hourly space velocity (GHSV). The reaction products were analyzed by on-line gas chromatography (HP 5890 GC) equipped with both TCD and FID detectors. GC column used is GS-Q 30 m manufactured by JW Scientific. A temperature program of 5° C./min to 300° C. was chosen for the analysis. Liquid products were collected in a cold trap at −3° C. and were also analyzed by GC-mass spectrometry. Carbon monoxide conversion and product selectivity were calculated on the basis of feed and product flow rates and carbon balance.

Figure 5:
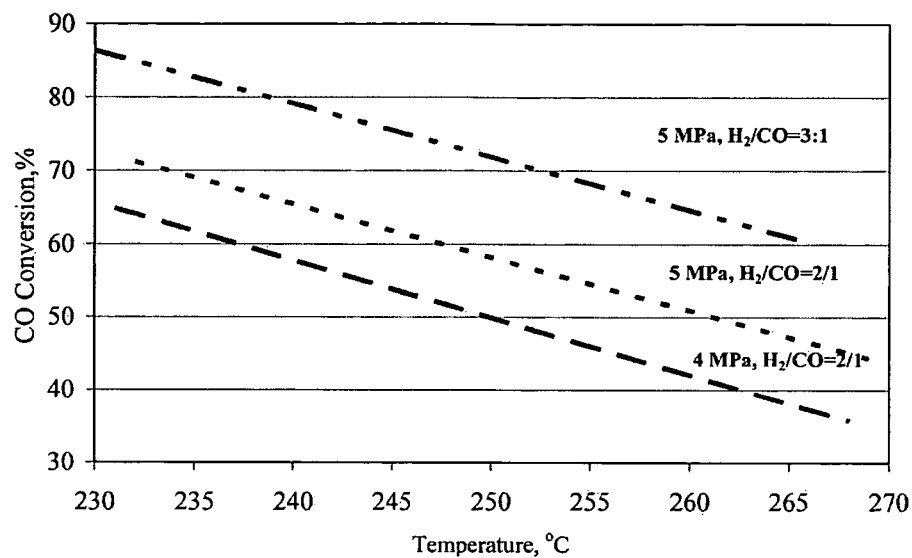
FIG. 5 illustrates an embodiment of syngas conversion to methanol: equilibrium CO conversion under different conditions; equilibrium is calculated for the reaction $CO+5H_2+CO_2=2CH_3OH+H_2O$.

Methanol synthesis is a thermodynamically limited process. As shown in FIG. 5, CO conversion decreases as the reaction temperature rises; yet it increases with higher pressure. Calculating the chemical equilibrium shows that the overall methanol yield can be increased, in principle, by combining the methanol synthesis with methanol dehydration. The calculation was done by coupling reactions (1) through (4) together. The combined reaction is expressed as $$CO+5H_2+CO_2 \rightarrow CH_3OCH_3+2H_2O$$

Figure 6:
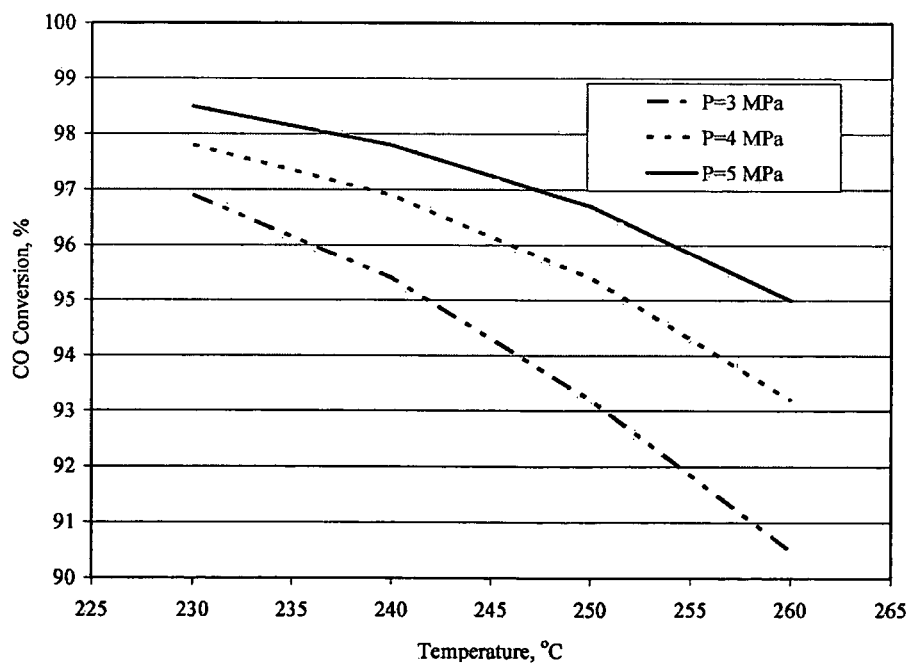
FIG. 6 illustrates an embodiment of direct syngas conversion to DME: CO equilibrium conversion under different conditions; equilibrium is calculated for the reaction $CO+5H_2+CO_2 \leftrightarrows CH_3OCH_3+2H_2O$.

FIG. 6 shows the results of integrating the two reactions. Synergy in total methanol production is obtained by effectively removing the products from the methanol synthesis reaction, i.e., by minimizing the reverse reaction. Consequently, maximum synergy is obtained close to the equilibrium limit for methanol synthesis where the reverse reaction rate is maximum.

A baseline test was conducted with the methanol synthesis catalyst. For this baseline test, methanol synthesis was performed over a commercial Cu-based catalyst at 3.8 MPa and GHSV=3000 to 15 000 $h^{-1}$. Steady state was achieved within 12 hours from startup. As shown in FIG. 7, CO conversion is lower at high GHSV. It becomes clear in FIG. 7 that CO conversion starts to level off and approaches equilibrium when GHSV is decreased from about 15 000 to about 3400 $h^{-1}$.

Figure 8:
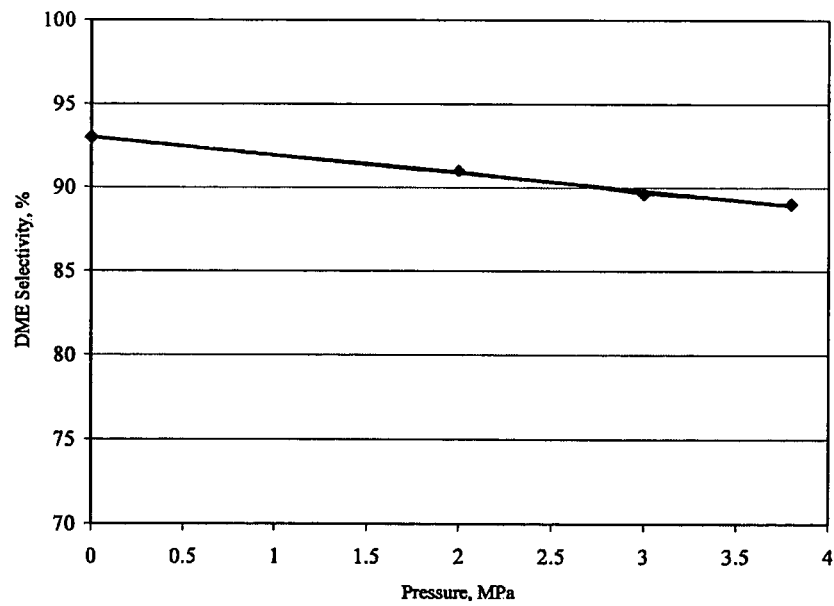
FIG. 8 illustrates the effect of pressure on dehydration of methanol in certain embodiments disclosed herein (H-ZSM-5 dehydration catalyst, T=234° C., GHSV=10 600 $h^{-1}$).

To better understand the performance of the combined processes in the microchannel reactor, the methanol dehydration reaction was carried out independently. It was speculated that the large quantity of water produced in both methanol synthesis and methanol dehydration reactions might retard the methanol dehydration activity. The inhibiting effect may become more severe at elevated pressure, because desorption of water is suppressed at high pressure, and active sites may be blocked for methanol absorption. Consequently, methanol dehydration was conducted at different pressures. As illustrated in FIG. 8, on raising pressure from ambient to 3.8 MPa, conversion of methanol to DME decreases, but not dramatically.

An important parameter in the design of a dual catalytic system is the catalyst loading ratio, that is, the methanol dehydration to methanol formation activity. Too high a methanol dehydration activity compared with water-gas shift activity leads to a high water production. Results shown in FIG. 9 indicate that CO conversion is affected by the catalyst ratio, but product selectivity is not sensitive to the change of catalyst ratio. A preferred catalyst ratio was found to be about 1:1 by weight.

Experiments were also conducted at GHSV=5000 $h^{-1}$, using two different feed compositions ($H_2$/CO=3:1 and 2:1). Pressure exhibited a positive effect on DME formation. As shown in FIG. 11, at low pressure of 1.0 MPa, low CO conversion occurs. A sharp increase in CO conversion is observed when pressure is increased from 1.0 to 3.8 MPa. The phenomenon observed in the study of pressure effect appears different from what has been reported in the literature where it has been indicated that, in DME synthesis, CO conversion increased with pressure but starts to level off at 2 MPa, beyond which the impact of pressure on CO conversion is not significant. Because the source of syngas, especially the type of reactor configuration, and the loading of two functionally independent catalysts are closely interrelated, the performance of DME synthesis in a microchannel reactor is different from conventional fixed-bed or slurry reactors.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:
1. A process for producing dimethyl ether comprising:
reacting syngas in contact with a hybrid catalyst in a microchannel reactor at a temperature from about 200° C. to about 400° C. with a contact time of from about 25 milliseconds to less than about 1 second; and converting more than about 60% of CO in the syngas to dimethyl ether and methanol.

2. The process of claim 1 comprising converting more than about 60% of CO in the syngas to dimethyl ether.

3. The process of claim 1, wherein there is no liquid holdup inside the microchannel reactor.

4. The process of claim 1, wherein the hybrid catalyst comprises a methanol synthesis catalyst and a methanol dehydration catalyst present in a weight ratio of about 1:1.

5. The process of claim 1, wherein the hybrid catalyst comprises a methanol synthesis catalyst and a zeolite catalyst present in a weight ratio of about 1:1 to about 2:1.

6. The process of claim 1, wherein the hybrid catalyst comprises F51-8PPT and ZSM-5 zeolite with a Si/Al ratio of about 30.

7. The process of claim 6, wherein the F51-8PPT and ZSM-5 zeolite are present in a weight ratio of about 1:1.

8. The process of claim 1, wherein the process is carried out in multiple microchannel reactors to produce greater than about 70% CO conversion to dimethyl ether and methanol.

9. The process of claim 1, wherein the process is carried out in multiple microchannel reactors to produce from about 80% CO conversion to about 88% CO conversion to dimethyl ether and methanol.

10. The process of claim 1, wherein the process is carried out at a temperature of from about 240° C. to about 290° C. with a contact time of less than about 500 milliseconds.

11. The process of claim 1, wherein the source of syngas is biomass.

12. A method of making DME, comprising: passing syngas in contact with a hybrid catalyst comprising a methanol synthesis catalyst and a dehydration catalyst in a microchannel reactor at a temperature of from about 240° C. to about 290° C. with a contact time of less than about 1 second and at a pressure in the range of about 0.5 MPa to about 8 MPa; and
producing greater than about 70% CO conversion to DME and methanol.

13. The process of claim 12, wherein the methanol synthesis and dehydration catalyst comprises a methanol synthesis catalyst and a zeolite catalyst that have been mixed together.

14. The process of claim 12, wherein the methanol synthesis and dehydration catalyst comprises a copper or palladium based methanol synthesis catalyst and a zeolite catalyst having a Si/Al ratio of about 30.

15. The process of claim 12, wherein the methanol synthesis and dehydration catalyst are present in a weight ratio of about 1:1 to about 2:1.

16. The process of claim 12, wherein the methanol synthesis and dehydration catalyst comprise a copper-based methanol synthesis catalyst and a zeolite catalyst present in a weight ratio of about 2:1 to about 1:1.

17. The process of claim 12, wherein the contact time is less than about 500 milliseconds and the pressure is from about 2 to about 8 MPa.

18. The process of claim 12, wherein the source of syngas is biomass.

19. A method of producing dimethyl ether, comprising:
providing a syngas source;
combining the syngas source with a hybrid catalyst comprising a methanol synthesis catalyst and a methanol dehydration catalyst; and
reacting the syngas in the presence of the catalyst in a microchannel reactor under substantially isothermal conditions at a temperature of from about 200° C. to about 350° C. with a contact time of from about 25 milliseconds to about 500 milliseconds to produce DME with greater than about 60% CO conversion to dimethyl ether and methanol.

20. A method of producing dimethyl ether, comprising:
providing a biomass syngas source;
combining the biomass syngas source with a methanol synthesis catalyst and dehydration catalyst, in a microchannel reactor, each microchannel at a single temperature of from about 200° C. to about 350° C. and with a contact time of less than about 1 second; and
producing greater than about 60% CO conversion to dimethyl ether and methanol.

21. A method of producing dimethyl ether, comprising:
providing a biomass syngas source;
combining the biomass syngas source with a methanol synthesis catalyst and zeolite catalyst present in a weight ratio of about 1:1; and reacting the biomass syngas in the presence of the catalyst in a microchannel reactor, at a temperature of from about 240° C. to about 290° C., the temperature varying less than about 2° C. while the biomass syngas is reacting in the microchannel reactor, and with a contact time of less than about 500 milliseconds; and
producing greater than about 60% CO conversion to dimethyl ether and methanol.

22. The process of claim 1 further comprising:
providing the syngas and the bydrid catalyst to a module including a plurality of microchannel reactors; and
reacting the syngas and the hybrid catalyst in the microchannel reactors at temperatures of from about 200° C. to about 350° C. and with a contact time of less than about 1 second to obtain greater than about 70% CO conversion to dimethyl ether and methanol.

* * * * *